United States Patent
Domenyuk et al.

(10) Patent No.: US 9,482,666 B2
(45) Date of Patent: Nov. 1, 2016

(54) HIGH THROUGHPUT SELECTION OF SPECIFIC CELL BINDING AND LYTIC POLYPEPTIDES

(71) Applicants: Valeriy Domenyuk, Tempe, AZ (US); Chris Diehnelt, Chandler, AZ (US); Stephen Johnston, Tempe, AZ (US)

(72) Inventors: Valeriy Domenyuk, Tempe, AZ (US); Chris Diehnelt, Chandler, AZ (US); Stephen Johnston, Tempe, AZ (US)

(73) Assignee: Arizona Board of Regents, a Body Corporate of the State of Arizona, Acting for and on Behalf of Arizona State University, Scottsdale, AZ (US)

( * ) Notice: Subject to any disclaimer, the term of this patent is extended or adjusted under 35 U.S.C. 154(b) by 218 days.

(21) Appl. No.: 14/359,389

(22) PCT Filed: Nov. 1, 2012

(86) PCT No.: PCT/US2012/063030
§ 371 (c)(1),
(2) Date: May 20, 2014

(87) PCT Pub. No.: WO2013/077982
PCT Pub. Date: May 30, 2013

(65) Prior Publication Data
US 2014/0315751 A1    Oct. 23, 2014

Related U.S. Application Data

(60) Provisional application No. 61/562,534, filed on Nov. 22, 2011.

(51) Int. Cl.
  *G01N 33/569* (2006.01)
  *C12Q 1/18* (2006.01)
  *G01N 33/50* (2006.01)
  *G01N 33/68* (2006.01)

(52) U.S. Cl.
  CPC ............... *G01N 33/569* (2013.01); *C12Q 1/18* (2013.01); *G01N 33/5008* (2013.01); *G01N 33/68* (2013.01)

(58) Field of Classification Search
  CPC .......... G01N 33/569; G01N 33/5008; G01N 33/68; C12Q 1/18
  USPC ......................................... 506/4
  See application file for complete search history.

(56) References Cited

U.S. PATENT DOCUMENTS

| | | | |
|---|---|---|---|
| 2005/0137136 A1* | 6/2005 | Petrenko | C07K 7/06 514/2.4 |
| 2005/0164380 A1* | 7/2005 | Trisler | C12N 5/0647 435/366 |
| 2008/0207522 A1 | 8/2008 | Hancock et al. | |
| 2011/0236429 A1 | 9/2011 | Hancock et al. | |
| 2012/0021967 A1 | 1/2012 | Johnston et al. | |
| 2012/0220540 A1 | 8/2012 | Johnston et al. | |

OTHER PUBLICATIONS

Husseneder et al., JoVE, 2010, pp. 1-6.*
Kim et al., Journal of Immunological Methods, Aug. 31, 2007, 325(1-2), pp. 51-66.*
(Continued)

*Primary Examiner* — Heather Calamita
*Assistant Examiner* — Karla Dines
(74) *Attorney, Agent, or Firm* — Quarles & Brady LLP; Gavin J. Milczarek-Desai

(57) ABSTRACT

The invention provides methods for identifying cell binding and/or lytic polypeptides that permit production of specific polypeptide therapeutics in a high throughput manner.

7 Claims, 10 Drawing Sheets

(56) References Cited

OTHER PUBLICATIONS

Giuliani et al., (2007). "Antimicrobial peptides: an overview of a promising class of therapeutics." Central European Journal of Biology 2(1): 1-33.
Wickens et al., (2008). "The association of early life exposure to antibiotics and the development of asthma, eczema and atopy in a birth cohort: confounding or causality?" Clinical & Experimental Allergy 38: 1318-1324.
Blaser, (2011). "Antibiotic overuse: Stop the killing of beneficial bacteria." Nature 476: 393-394.
Chambers et al., (2009). "Waves of resistance: *Staphylococcus aureus* in the antibiotic era." Nat. Rev. Micro. 7: 629-641.
Hawkey et al., (2009). "The changing epidemiology of resistance." Journal of Antimicrobial Chemotherapy 64, Suppl. 1: i3-i10.
Teuber, (2001). "Veterinary use and antibiotic resistance." Current Opinion in Microbiology 4: 493-499.
Cohen, (1992). "Epidemiology of Drug Resistance: Implications for a Post-Antimicrobial Era." Science 257: 1050-1055.
Silver et al., (1993). "Discovery and development of new antibiotics: the problem of antibiotic resistance." Antimicrob. Agents Chemother. 37: 377-383.
Casadevall, (1996). "Crisis in Infectious Diseases: Time for a New Paradigm?" Clinical Infectious Diseases 23: 790-794.
Legutki et al., (2010). "A general method for characterization of humoral immunity induced by a vaccine or infection." Vaccine 28: 4529-4537.
Saylor et al., (2009). "Monoclonal antibody-based therapies for microbial diseases." Vaccine 27: G38-G46.
Reichert et al., (2006). "Anti-infective monoclonal antibodies: perils and promise of development." Nat. Rev. Drug Discov. 5: 191-195.
Diehnelt et al., (2010). "Discovery of High-Affinity Protein Binding Ligands—Backwards." PLoS One 5: e10728.
Yeaman et al., (2003). "Mechanisms of Antimicrobial Peptide Action and Resistance." Pharmacological Reviews 55: 27-55.
Zhang et al., (2005). "Antimicrobial Peptide Therapeutics for Cystic Fibrosis." Antimicrob. Agents Chemother. 49: 2921-2927.
Bradshaw, (2003). "Cationic Antimicrobial Peptides: Issues for Potential Clinical Use." BioDrugs 17: 233-240.
Dhople et al., (2006). "The human beta-defensin-3, an antibacterial peptide with multiple biological functions." Biochimica et Biophysica Acta 1758: 1499-1512.
Zasloff, (1987). "Magainins, a class of antimicrobial peptides from Xenopus skin: isolation, characterization of two active forms, and partial cDNA sequence of a precursor." Proceedings of the National Academy of Sciences 84: 5449-5453.
Sawai et al., (2002). "Impact of single-residue mutations on the structure and function of ovispirin/novispirin antimicrobial peptides." Protein Engineering 15: 225-232.
Srinivas et al., (2010). "Peptidomimetic Antibiotics Target Outer-Membrane Biogenesis in Pseudomonas aeruginosa." Science 327: 1010-1013.
Chou et al., (2008). "Design and synthesis of cationic antimicrobial peptides with improved activity and selectivity against *Vibrio* spp." International Journal of Antimicrobial Agents 32: 130-138.
Gordon et al., (2005). "A Review of Antimicrobial Peptides and Their Therapeutic Potential as Anti-Infective Drugs." Current Eye Research 30: 505-515.
Cudic et al., (2002). "Development of novel antibacterial peptides that kill resistant isolates." Peptides 23: 2071-2083.
Tencza et al., (1999). "Lentivirus-derived antimicrobial peptides: increased potency by sequence engineering and dimerization." Journal of Antimicrobial Chemotherapy 44: 33-41.
Wang et al., (2009). "APD2: the updated antimicrobial peptide database and its application in peptide design." Nucleic Acids Research 37: D933-D937.
Hancock et al., (2006). "Antimicrobial and host-defense peptides as new anti-infective therapeutic strategies." Nat. Biotech. 24: 1551-1557.
Eckert et al., (2006). "Adding Selectivity to Antimicrobial Peptides: Rational Design of a Multidomain Peptide against *Pseudomonas* spp." Antimicrob. Agents Chemother. 50: 1480-1488.
He et al., (2010). "Systematic Approach to Optimizing Specifically Targeted Antimicrobial Peptides against *Streptococcus mutans*." Antimicrob. Agents Chemother. 54: 2143-2151.
Morales Betanzos et al., (2009). "Bacterial Glycoprofiling by Using Random Sequence Peptide Microarrays." ChemBioChem 10: 877-888.
Halperin et al., (2010). "Exploring Antibody Recognition of Sequence Space through Random-Sequence Peptide Microarrays." Molecular & Cellular Proteomics 10.
Reddy et al., (2005). "Protein "fingerprinting" in complex mixtures with peptoid microarrays." Proceedings of the National Academy of Sciences of the United States of America 102: 12672-12677.
Hilpert et al., (2005). "High-throughput generation of small antibacterial peptides with improved activity." Nat Biotech 23: 1008-1012.
Hilpert et al., (2009). "Screening and Characterization of Surface-Tethered Cationic Peptides for Antimicrobial Activity." Chemistry & Biology 16: 58-69.
Hsu et al., (2006). "Analyzing the dynamic bacterial glycome with a lectin microarray approach." Nat. Chem. Biol. 2: 153-157.
Disney et al., (2004). "The Use of Carbohydrate Microarrays to Study Carbohydrate-Cell Interactions and to Detect Pathogens." Chemistry & Biology 11: 1701-1707.
Falsey et al., (2001). "Peptide and Small Molecule Microarray for High Throughput Cell Adhesion and Functional Assays." Bioconjugate Chemistry 12: 346-353.
Palacios et al., (2007). "Panmicrobial oligonucleotide array for diagnosis of infectious diseases." Emerging infectious diseases 13: 73-81.
Liu et al., (2009). "A High Speed Detection Platform Based on Surface-Enhanced Raman Scattering for Monitoring Antibiotic-Induced Chemical Changes in Bacteria Cell Wall." PLoS One 4: e5470.
CLSI, (2009). "Methods for dilution antimicrobial susceptibility tests for bacteria that grow aerobically; Approved standard-Ninth Edition." CLSI document M07-A9, vol. 32 No. 2.
Svarovsky et al., (2011). "High-throughout platform for rapid deployment of antimicrobial agents." ACS Combinatorial Science 13: 634-638.
Takeshi et al., (2009). "Signal-to-noise ratio improvement of peptide microarrays by using hyperbranched-polymer materials." J. Appl. Phys. 105: 102020.
Hong et al., (2004). "Mesospaced surface for DNA micro-array and other applications." Proceedings of SPIE 5593: 232-246.
Van Rooijen et al., (2010). "Membrane permeabilization by oligomeric [alpha]-synuclein: in search of the mechanism." PLoS One 5(12): e14292.
Huo et al., (2011). "Antimicrobial and DNA-binding activities of the peptide fragments of human lactoferrin and histatin 5 against *Streptococcus mutans*." Archives of oral biology 56: 869-876.
Domenyuk et al., (2011). "High-throughput selection of new antimicrobials with random sequence peptide microarrays." Drug Discovery Chemistry 1-13.
Casadevall, (2009). "The case for pathogen-specific therapy." Expert Opinion on Pharmacotherapy 10: 1699-1703.
Kim et al., (2007). "Potential Ecological and Human Health Impacts of Antibiotics and Antibiotic-Resistant Bacteria from Wastewater Treatment Plants." Journal of Toxicology and Environmental Health, Part B 10: 559-573.
Sitaram et al., (2002). "Host-defense Antimicrobial Peptides: Importance of Structure for Activity." Current Pharmaceutical Design 8: 727-742.

\* cited by examiner

SEQUENCE LISTING

<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: Synthetic

```
<400> SEQUENCE: 1

Arg Trp Arg Arg His Lys His Phe Lys Arg Pro His Arg Lys His Lys
1               5                   10                  15

Arg Gly Ser Cys
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic

<400> SEQUENCE: 2

Asp Arg Ile Phe His Lys Met Gln His Lys Pro Tyr Lys Ile Lys Lys
1               5                   10                  15

Arg Gly Ser Cys
            20
```

HIGH THROUGHPUT SELECTION OF SPECIFIC CELL BINDING AND LYTIC POLYPEPTIDES

CROSS-REFERENCE

This Application is a 371 application of PCT/US2012/063030 filed Nov. 1, 2012, which claims priority to U.S. Provisional Patent Application Ser. No. 61/562,534 filed Nov. 22, 2011, incorporated by reference herein in their entirety.

STATEMENT OF U.S. GOVERNMENT INTEREST

This work was funded by grant number W911NF-10-1-0299 awarded by the Defense Advanced research Projects Agency. The U.S. government has certain rights in the invention.

BACKGROUND

Antimicrobial resistance of bacteria is rapidly increasing and has been declared a multinational public health crisis. Thus, there is a need for a new generation of therapeutics which are (i) less prone to development of resistance in microbes and (ii) more specific to the target(s) of interest. Natural antimicrobial peptides (AP) are well known as a part of the innate immune system and have been extensively studied. Despite the overall enthusiasm, since 1945 there were just a few commercial products based on AP and for topical use only. The majority of AP based research and development has been limited to naturally occurring AP's or their derivatives. In turn, natural AP's are evolutionary optimized to be toxic and share a broad mechanism of action.

SUMMARY OF THE INVENTION

The present invention provides methods for identifying cell binding and/or lytic polypeptides, comprising
(a) contacting one or more addressable polypeptide arrays with:
  (i) a first population of cells of interest comprising an intracellular detectable marker (IDM); and
  (ii) a second population of the cells of interest comprising a cell surface detectable marker (CSDM);
  wherein the addressable polypeptide arrays comprises at least 1000 polypeptides of between 15-24 amino acids in length in defined locations on the array(s), and wherein the contacting occurs under conditions suitable to promote binding of polypeptides to the cells of interest; and
(b) detecting binding of the polypeptides to the cells of interest; wherein a polypeptide that binds cells in the first population of cells without damage to the cells and binds cells in the second population of cells without damage to the cells is a binding polypeptide for the cells of interest; and wherein a polypeptide that binds cells in the first population of cells with damage to the cells and binds cells in the second population of cells with damage to the cells is a lytic polypeptide for the cell of interest.

In one embodiment, the methods comprise using at least two polypeptide arrays, wherein the first population of cells is contacted to the first polypeptide array and the second population of cells is contacted to the second polypeptide arrays. In another embodiment, the IDM is a fluorescent chloromethyl derivative. In a further embodiment, a surface of the addressable polypeptide arrays is functionalized by a process comprising:
  (i) treating the surface with 3-glycidoxypropyl-trimethoxysilane to create a treated surface;
  (ii) reacting the treated surface with hyperbranched polyethylenimine to create a reacted surface; and
  (iii) further reacting the surface with heterobifunctional crosslinker succinimidyl-4-(N-maleimidomethyl)cyclohexane-1-carboxylate;
wherein the polypeptides are bound to the functionalized surface.

In various further embodiments, the cells may be pathogenic cells, including but not limited to bacterial cells, protozoan cells, fungal cell, and helminth cells, or may be tumor cells.

In another embodiment, the methods further comprise preparing a synthetic antibody by linking (a) a binding polypeptide for a cell of interest; and (b) a lytic polypeptide for the cell of interest. In a further embodiment, the methods further comprise identifying a polypeptide binding profile for a cell of interest.

DETAILED DESCRIPTION OF THE INVENTION

Figure 1A:
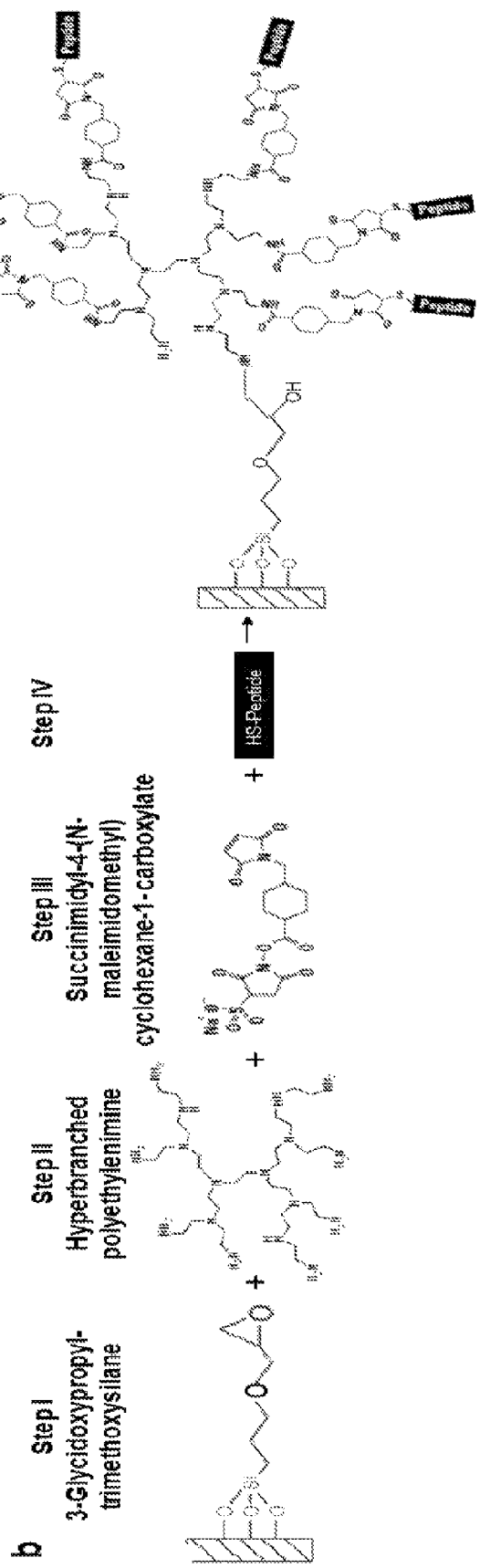
FIG. 1. (a) Peptide microarray polymer surface chemistry specifically designed for bacterial cells binding. (b) Scheme of binding and competition assays to control bacterial cell adhesion to the peptides on microarrays. (c) Functional assay to select peptide-binders and antimicrobial peptides directly on peptide microarrays. Bacteria of interest are applied to the peptide microarray carrying dyes either in cytoplasm or on the membrane. Intracellular stain "Cell Tracker Orange" (CTO) gives the signals at the peptides which bind bacterial cells without harm and absent at the peptides disrupting membranes. Outer membrane label "Alexa Fluor 555" presents in both cases. Comparing the staining/labeling profiles of certain pathogen at the same peptide sequence allows selection of peptides either with binding or lytic activity.

All references cited are herein incorporated by reference in their entirety. Within this application, unless otherwise stated, the techniques utilized may be found in the examples that follow, and/or any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of the invention can be combined unless the context clearly dictates otherwise.

In a first aspect, the present invention provides methods for identifying cell binding and/or lytic polypeptides, comprising
(a) contacting one or more addressable polypeptide arrays with:
 (i) a first population of cells of interest comprising an intracellular detectable marker (IDM); and
 (ii) a second population of the cells of interest comprising a cell surface detectable marker (CSDM);
 wherein the addressable polypeptide arrays comprises at least 1,000 polypeptides of between 15-24 amino acids in length in defined locations on the array(s), and wherein the contacting occurs under conditions suitable to promote binding of polypeptides to the cells of interest;
(b) detecting binding of the polypeptides to the cells of interest; wherein a polypeptide that binds cells in the first population of cells without damage to the cells and binds cells in the second population of cells without damage to the cells is a binding polypeptide for the cells of interest; and wherein a polypeptide that binds cells in the first population of cells with damage to the cells and binds cells in the second population of cells with damage to the cells is a lytic polypeptide for the cell of interest.

As shown in the examples that follow, the methods can be used to readily identify binding and/or lysis activity of polypeptides on the array, for potential use in a wide variety of applications, including but not limited to development of synthetic antibodies with enhanced specificity for pathogenic cellular organisms of interest, and anti-tumor cell polypeptides. Furthermore, the methods allow selection of candidates for making specific synthetic antibodies, such as pathogen-specific (or tumor-specific) synthetic antibodies, which is especially important in the light of growing antimicrobial resistance to current antibiotics. Such specific synthetic antibodies will permit curing target pathogen, will not harm the commensal flora and will not trigger the rise and spread of resistant pathogenic strains.

The method is high-throughput, inexpensive, simple, and can be used with any suitable library of polypeptides. The methods can also be used, for example, in identifying a polypeptide binding profile for a cell of interest, which can be used in, for example, diagnostics or environmental testing. The addressable polypeptide arrays comprises at least 1,000 polypeptides; in other embodiments, at least 2000; 3000; 4000; 5000; 6000; 7000; 8000; 9000; or 10,000 polypeptides.

The polypeptide array comprises a surface to which the polypeptides are bound; it is addressable, meaning that the polypeptides are present at defined locations, to facilitate identification of polypeptides exhibiting desired binding and/or lytic activity. Any suitable surface can be used, including but not limited to microarrays, beads, columns, optical fibers, wipes, nitrocellulose, nylon, glass, quartz, diazotized membranes (paper or nylon), silicones, polyformaldehyde, cellulose, cellulose acetate, paper, ceramics, metals, metalloids, semiconductive materials, coated beads, magnetic particles; plastics such as polyethylene, polypropylene, and polystyrene; nanostructured surfaces; nanotubes (such as carbon nanotubes), and nanoparticles (such as gold nanoparticles or quantum dots. In a preferred embodiment, the surface comprises a glass of plastic surface, such as a glass or plastic microscope slide.

The polypeptide can be directly linked to the surface, or attached to the surface via a linker. Thus, the substrate and/or the polypeptides can be derivatized using methods known in the art to facilitate binding of the polypeptides to be assessed to the solid support, so long as the derivitization does not eliminate detection of binding between the polypeptides and the cells. A variety of different materials may be used to prepare the surface to obtain various properties. For example, proteins (e.g., bovine serum albumin) or mixtures of macromolecules (e.g., Denhardt's solution) can be used to minimize non-specific binding, simplify covalent conjugation, and/or enhance signal detection. If covalent bonding between the polypeptides and the surface is desired, the surface of the substrate will usually be functionalized or capable of being functionalized. Functional groups which may be present on the substrate surface and used for linking include, but are not limited to, carboxylic acids, aldehydes, amino groups, cyano groups, ethylenic groups, hydroxyl groups, and thiol groups. In addition, strong, but noncovalent, interactions may be used for affixing the molecules to the substrate surface (e.g., attachment via a biotin/avidin linkage). Methods for linking polypeptides to various surfaces are well known to those of skill in the art.

The surface can be functionalized in any suitable way to optimize cell adhesion to polypeptides. Based on the teachings herein, it is within the level of skill in the art to determine appropriate means for optimizing cell adhesion to the polypeptides. In one embodiment, described in more detail in the examples that follow, the surface is functionalized with 3-glycidoxypropyl-trimethoxysilane, which is then reacted with hyperbranched polyethylenimine, followed by reacting the surface with heterobifunctional cross-linker succinimidyl-4-(N-maleimidomethyl)cyclohexane-1-carboxylate. The polypeptides are then bound to the functionalized surface. Examples of this embodiment are provided below.

The first and second populations of cells are the same cell type. Any suitable cell type for which binding and/or lytic polypeptides are desirable can be used in the methods of the invention. In a preferred embodiment, the cells are pathogenic cells. In a further preferred embodiment, the pathogenic cells are selected from the group consisting of bacterial cells, protozoan cells, fungal cell, and helminth cells. The examples below demonstrate an exemplary use of the methods with bacterial cells. Binding and lytic polypeptides that target bacterial cells can be used, for example, as antibiotics (alone (lytic polypeptides), or in combination (ex: synthetic antibodies comprising linked binding and lytic polypeptides) and for coating surfaces in hospitals as well as medical instruments and devices. In another preferred embodiment, the cells are tumor cells, such as cells derived from a human tumor. Binding and lytic polypeptides that target tumor cells can be used, for example, in anti-tumor therapy (alone (lytic polypeptides), or in combination (ex: synthetic antibodies comprising linked binding and lytic polypeptides), or tumor cell detection (ex: binding polypeptides).

The IDM can be any suitable intracellular marker with limited leakage from intact cells, and the CSDM can be any suitable type that binds to the cell surface with limited ingress into cells. Exemplary IDM and CSDM types include, but are not limited to, radioisotope labeled markers, fluorescently labeled markers, luminescently labeled markers, and electrochemically labeled markers (ie: ligand labels with different electrode mid-point potential, where detection comprises detecting electric potential of the label). In a preferred embodiment, fluorescently labeled markers are used. Specific IDMs and CSDMs for use in a given assay will depend on the cells being used, the surface and its functionalization, etc. Based on the teaching of the present application, one of skill in the art can determine an appropriate IDM and CSDM for a given assay. In one preferred embodiment, the IDM is a fluorescent chloromethyl derivative, which is processed into membrane impermeable compounds that are retained inside the cells up to 72 hours after loading, such as those available from Invitrogen (Cell-Tracker™ probes). In one embodiment, the IDM comprises Xanthylium, 9-[2-carboxy-4(or 5)-[[4-(chloromethyl)benzoyl]amino]phenyl]-3,6-bis(dimethylamino) (i.e.: Cell-Tracker™ Orange), or functional equivalents thereof. In another embodiment, the CSDM is any marker with an amino-reactive functional group, including but not limited to those disclosed herein.

The methods comprise detecting binding of the polypeptides to the cells of interest. Any suitable means can be used for detecting binding of the polypeptides; a specific means will depend on the marker types being used. For example, fluorescent array readers are well known in the art, as are instruments to record electric potentials on a substrate (For electrochemical detection see, for example, J. Wang (2000) *Analytical Electrochemistry, Vol.*, 2nd ed., Wiley—VCH, New York). Based on the teaching of the present application, one of skill in the art can determine an appropriate detection means for a given assay. Exemplary detection means are disclosed in the examples that follow.

One or more addressable polypeptide arrays are contacted with the populations of cells. Thus, in one embodiment, a single array can be used, where the array comprises at least two separately addressable but identical sets of at least 10,000 polypeptides on the array surface. In this embodiment, the IDM and the CSDM used are distinguishable, such as different wavelength dyes that are distinguishable using a suitable fluorescence detection technique. In another embodiment, at least two separate arrays (a first array and a second array) are used that each comprise identical sets of the at least 10,000 polypeptides on the array surface, and the first population of cells is contacted with the first array and the second population of cells is contacted with the second array.

The contacting occurs under any conditions suitable to promote binding of polypeptides to the cells of interest. It is well within the level of skill in the art, based on the teachings herein, to determine appropriate binding conditions for use in a given assay. The examples below provide exemplary conditions for use with bacterial cells. In various embodiments, the conditions may include one or more of (i) blocking of the slides prior to cell binding to limit non-specific binding; (ii) use of cell binding competitors, such as mouse or human serum for and (iii) use of detergent (including but not limited to Tween20) in the binding solution Wash steps to remove non-binding cells can be utilized as appropriate/desirable for a given assay.

In a preferred embodiment, the methods further comprise contacting one or more identical arrays with a third population of the cells of interest, wherein the third population includes both the labeled cells and an excess of unlabeled cells. This embodiment can be used, for example, to minimize false positives resulting from marker binding. For example, where a single array is used for binding of the first and second population of cells, a second array, identical to the first array is contacted with a mixture of labeled cells plus excess unlabeled cells (for example, a 10-50-fold increase of unlabeled compared to labeled cells; alternatively, 15-30, or about a 20× excess of unlabeled cells).

Similarly, if two arrays are used for binding of the first and second population of cells, third and fourth identical arrays are contacted with the mixture of labeled cells plus excess unlabeled cells. Any other suitable controls can be used as most appropriate for a given assay.

The polypeptides on the array may be of any type: naturally occurring, non-naturally occurring, or a combination. In a preferred embodiment, the polypeptides are non-naturally occurring. The polypeptides may include non-naturally occurring amino acids, and may comprise D amino acids, L amino acids, or a combination of D and L amino acids, and may comprise amino acid analogues. The polypeptides may be present at any suitable density on the array. As will be understood by those of skill in the art based on the teachings herein, preferred polypeptide densities will differ depending on the size of cells to be contacted to the array. It is preferred that at least about 50-100 cells are bound to a polypeptide location ("spot') on the array. In one non-limiting embodiment, the cell to be contacted to the array is $E.\ coli$, and a diameter of the polypeptide spot on the array is at least about 100 um-150 um to permit detection of binding at specific spots on the array. Based on the teachings herein, those of skill in the art can determine appropriate polypeptide densities based on the cell to be contacted to the array. In various embodiments, the array has a polypeptide density of at least 0.5 to $1\times10^5$ peptides/um$^2$, preferably at least 2.5 to $5\times10^5$ peptides/um$^2$, more preferably 5 to $10\times10^5$ peptides/um$^2$, or more, up to, for example, $1\text{-}1.5\times10^9$ peptides/um$^2$. In one embodiment, each spot on the array has a polypeptide concentration of between about 0.01 mg/ml to about 5 mg/ml. In various other embodiments, the polypeptide concentration per spot is 0.05 mg/ml to about 2.5 mg/ml; 0.1 mg/ml to about 2 mg/ml; 0.5 mg/ml to about 1.5 mg/ml; 0.75 mg/ml to about 1.25 mg/ml; or about 1 mg/ml.

Polypeptides on the array are 15-24 amino acids in length; in various embodiments, they are 16-24, 17-24, 18-24, 19-24, 20-24, 15-23, 16-23, 17-23, 18-23, 19-23, 20-23, 15-22, 16-22, 17-22, 18-22, 19-22, 20-22, 15-21, 16-21, 17-21, 18-21, 19-21, 20-21, 15-20, 16-20, 17-20, 18-20, 19-20, or 20 amino acids in length.

The methods of the invention permit identification of polypeptides that bind to cells without damaging (i.e.: lysing or otherwise disrupting the cell membrane) the cells (ie: "binders"), and simultaneous identification of polypeptides that bind to the same cell type and damage (i.e.: lyse or otherwise disrupt the cell membrane) the cells ("lytic polypeptides"). The methods thus may further comprise carrying out any suitable validation study of polypeptides identified as binders or lytic polypeptides. Any suitable validation studies can be used; it is well within the level of those of skill in the art, based on the teachings herein, to determine an appropriate validation study for a given polypeptide identified as a binder and/or a lytic polypeptide against a cell type of interest. In one embodiment, validation studies comprise conducting in vitro assays to show binding specificity and/or strong lytic activity of a polypeptide for a cell of interest. In another embodiment, a polypeptide of interest identified by the methods of the invention is modified to improve binding specificity and/or lytic activity for a cell of interest. Exemplary such validation studies are provided below in the context of bacterial cells.

The functional assays of the invention provide an unlimited source of cell-specific peptides identified as "binders," which can be conjugated with lytic polypeptides, resulting in chimeric dual-function compounds (synthetic antibodies) with specificity assigned against certain cell types. Thus, the methods further comprise preparing a synthetic antibody by linking
(a) a binding polypeptide for a cell of interest; and
(b) a lytic polypeptide for the cell of interest.

In this embodiment, it is preferred that the binding polypeptide shows binding specificity for a target cell of interest, such as a pathogen. The lytic polypeptide can have a broad spectrum of activity, since the binding polypeptide will serve to provide specificity of the synthetic antibody to the target cell. The methods of this embodiment can thus be used, for example, to prepare synthetic antibodies against a pathogen of interest, such as a bacterial cell, or against a tumor cell, such cells derived from a human tumor.

EXAMPLES

Strategy Outline

Our ultimate goal was to find a method for making alternative antibacterial therapeutics that possess specific activity for a particular pathogen. In order to cover diverse pathogens, we explored the screening of entire cells with peptide microarrays rather than profiling single species of surface molecules. Lipoteichoic acids, surface proteins and peptidoglycans could conceivable be the targets for peptides in Gram positive (G+) bacterial membranes while LPS is the most likely target in Gram negative (G−). To ensure diversity of surface components we selected the following model bacteria: pathogenic G− $E.\ coli$ O111:B4 (EC) and $Pseudomonas\ aeruginosa$ (PA); G+$Streptococcus\ mutans$ (SM) and $Staphylococcus\ aureus$ (SA) and non-pathogenic G+$Bacillus\ subtilis$ (BS).

Figure 1B:
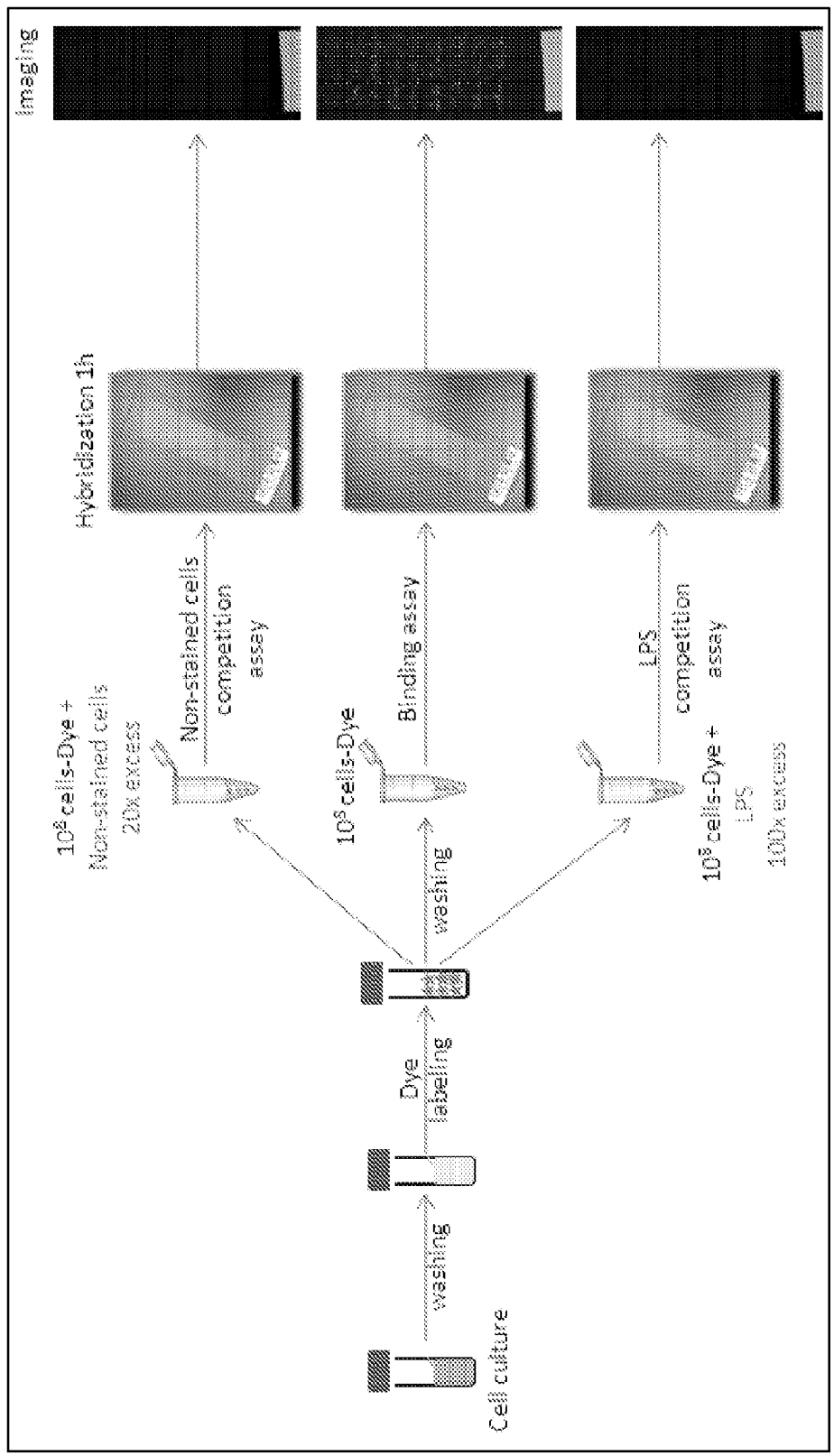

The basic strategy was to prepare a given bacteria (entire cells) so that it fluoresces, incubate it with the peptide microarray, and measure fluorescence as a proxy for the total number of intact bacteria per peptide spot (each spot is 150±36 um in diameter). To ensure bacterial cell adhesion, we developed a polymer microarray surface chemistry (FIG. 1a). The polymer allowed far higher densities of peptides and prevented non-specific binding to areas where no peptides were attached. This approach provided a set of peptides with binding specificity for a given bacteria, but without obvious therapeutic effect. In order to enhance the selection of therapeutic candidates, we developed a protocol for distinguishing peptides with direct antimicrobial action (lytic) from peptides that bind bacteria without harm (FIG. 1b, c). After appropriate in vitro validation, lead specific binding peptides and broad spectra lytic peptides were to be combined in a hybrid dual function molecule (synthetic antibody) with specificity assigned against a particular pathogen.

Bacterial Cells Adhesion to the Peptide Microarrays

Figure 2A:
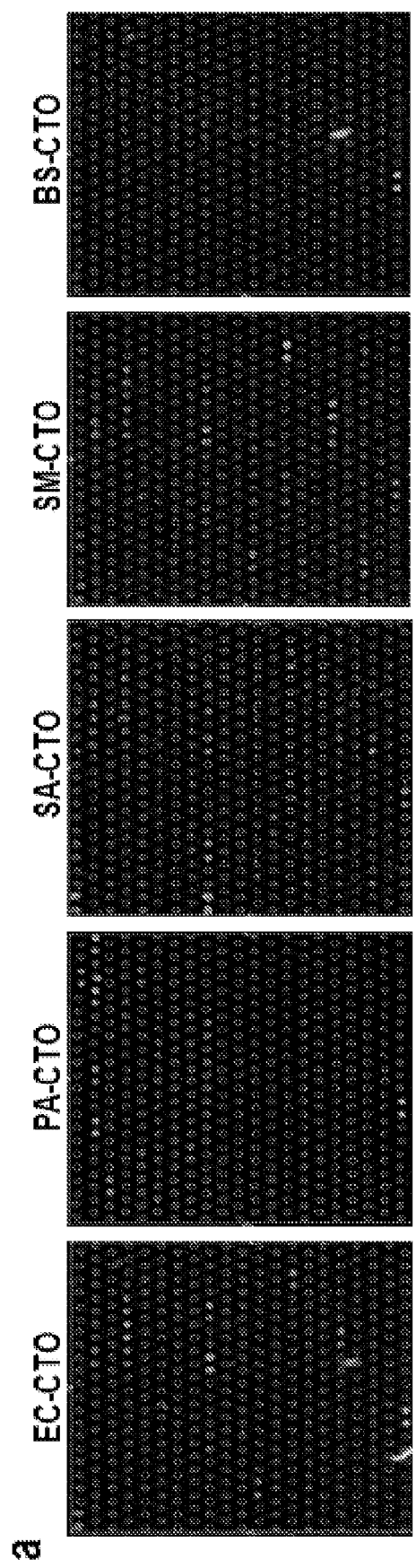
FIG. 2. Efficacy of polymer 10K random sequence peptide microarrays for screening of bacteria. (a) Distinct profiles of CTO stained $E.\ coli$ O111:B4 (EC), $P.\ aeruginosa$ (PA), $S.\ aureus$ (SA), $S.\ mutans$ (SM), $B.\ subtilis$ (BS) on representative subarray (⅛ of 10K). Cell binding signals are depicted as a false color (green) in the GenPix Pro software. (b) Detection of specific peptide-binders for bacterial cells. Binding data of CTO stained bacteria (x axes) plotted vs negative controls (y axes): 1, 3, 4—competition with excess on non-labeled cells; 2—competition with excess of free LPS. Both axes show raw median fluorescent signal at 543 nm on a logarithmic scale. Green lines delimit the twofold change. Peptide-binders for bacteria are selected out of twofold change on x axes as those where CTO-cells were competed with excess of non-stained cells. Annotated dark dots are peptide-binders for EC selected in 1. Analyzed at 2, these peptides show LPS as the main target of Gram negative strains for peptide binders (more binders detected with LPS as a competitor). Analyzed at 3 and 4, annotated peptides show that different strains have specific profiles (only about ⅓ of EC's binders repeated in profiles of SM and SA). Peptide named in 1 were re-synthesized and printed on custom array for fluorescent microscopy. (c) Bacterial cell adhesion to the peptides on polymer microarray detected with fluorescent microscopy. Upper image is negative control (non-binding peptide EFSN). Others are peptide-binders for EC selected in binding/competition assay (see b1). Scale—100 um.

DNA intercalating dyes SYTO 9 and DRAQ 5 used initially were leaching from bacterial cells resulting in false positive signals. They were replaced with Cell Tracker Orange (CTO) which is activated upon entry to a bacterial cell and then becomes cell-impermeant in intact cells. Using polymer slides and CTO fluorescent labeling we conducted binding assays for EC, PA, SA, SM and BS bacteria and obtained distinct microarray profiles (FIG. 2a). Each experiment was done in triplicate with correlation coefficients across replicas typically >0.96. The raw images represent the same area of five peptide microarrays processed with different bacterial strains (FIG. 2a).

Figure 2B:
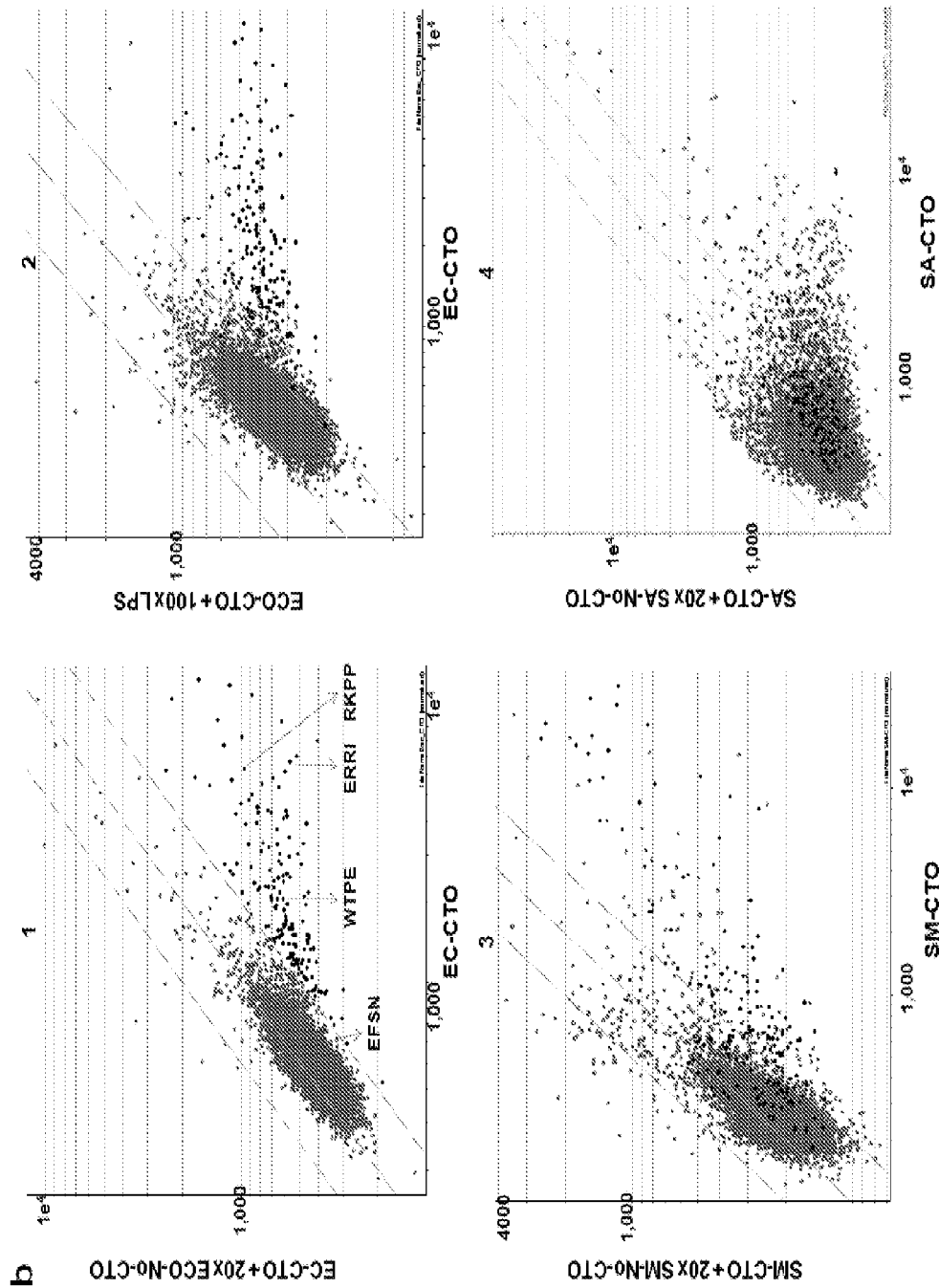

To subtract possible non-specific and false-positive signals, we developed competition assays as profiling of CTO-labeled cells mixed with 20× excess of un-labeled cells of the same strain. The scatter plots[31,33] (FIG. $2b_{1,2,3,4}$) illustrate distribution of fluorescent intensities obtained in each binding assay against those from the corresponding competition assay for a particular strain. Points that exceed twofold difference compared to the competition are shown as an elongated pattern of points extending along x-axis (black filled circles on FIG. 2b). This set of signals is definitely driven by fluorescent bacteria bound to a certain peptide. Such a representation clearly shows both the efficacy of our surface chemistry and the competition assays that remove non-informative binding. Competition assays are straightforward protocols for G− bacteria (FIG. $2b_{1,2}$) as well as for G+ (FIG. $2b_{3,4}$). Profiling G− bacteria could be also done with alternative competitor—their free LPS (FIG. $2b_2$). It was demonstrated that 99% of EC peptide-binders selected with un-labeled cells competition repeated on the scatter plot with LPS competition (see EC, FIG. $2b_{1,2}$). This showed that molecules other than LPS are unlikely to participate substantially in the interaction of G− bacterial cells with peptides.

In order to demonstrate the ability of polymer peptide microarrays to discriminate different pathogen strains, the list of peptide-binders selected for EC (annotated black filled circles, FIG. $2b_1$) was examined on SM and SA plots (FIG. $2b_{3,4}$). Only ~⅓ of peptide-binders appeared to be common across all tested strains while others were unique and could be considered as candidates for specific therapeutic agents. Comparison of binders for bacteria within G+ (SA, SM and BS) and G− (EC and PA) groups showed that each strain has specific peptides to which they bind. These data confirm that a peptide library containing 10,000 random sequence peptides is sufficiently rich in ligands to allow multiple different bacterial strains to bind specifically.

Figure 2C:
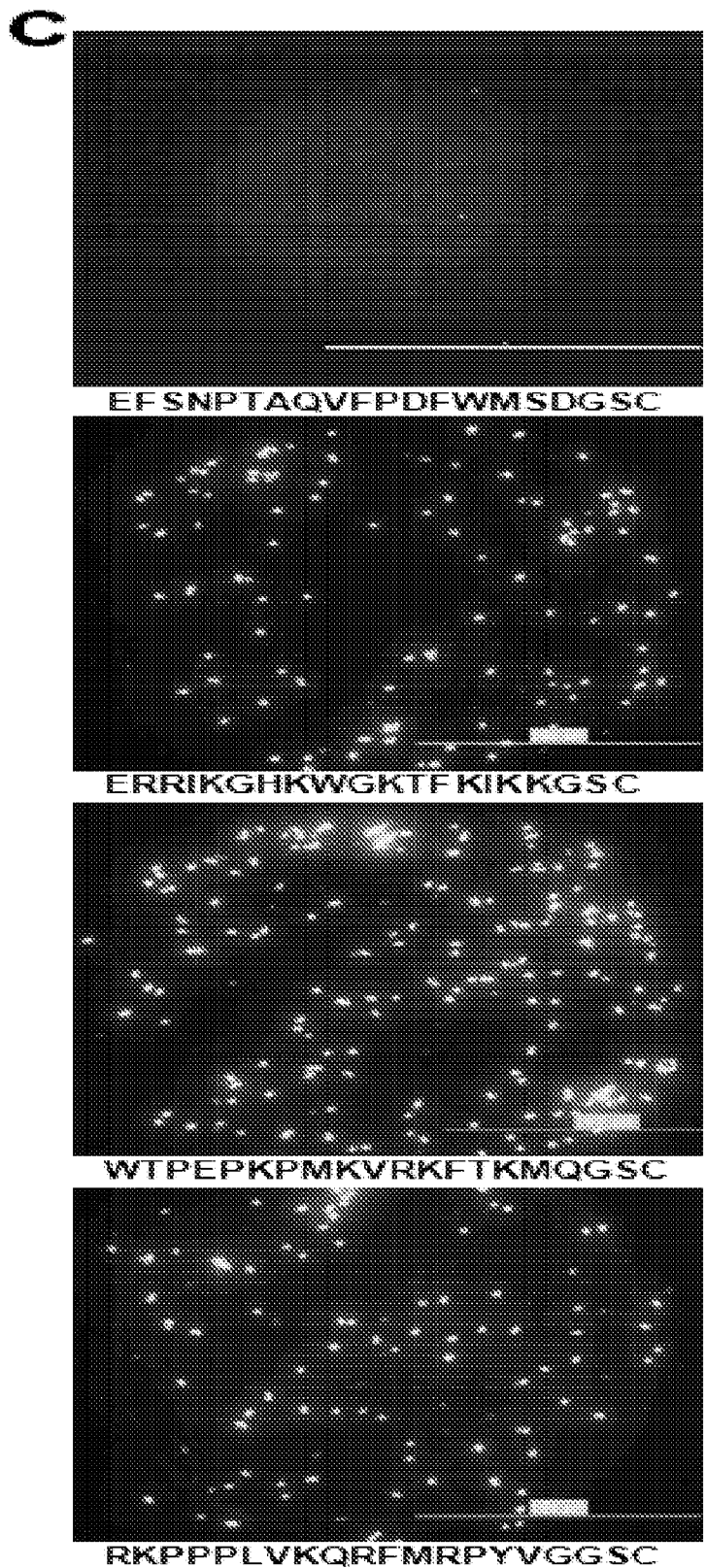

To further assess the bacterial cell adhesion to the peptides on microarray, we conducted more precise visualization with fluorescent microscopy (see EC, FIG. 2c). To restrict the test conditions, the 15 random peptides that showed the ability to bind EC cells on a microarray were re-synthesized, HPLC purified and printed on custom polymer slides. These precautions were to estimate the rate of false positives which could be caused by errors in peptide sequences, impurities, synthesis yield or efficiency of the 10K peptides originally printed on the microarray. Adhered bacterial cells are seen in FIG. 2c. All of the tested peptide proved their binding ability after re-synthesis.

These methods allowed us unambiguous detection of bacterial cell adhesion to the peptides on microarray and ensured selection of specific peptide-binders for a particular strain.

Functional Assay

We assume three possible classes of peptides with respect to their abilities to interact with bacteria: 1) Peptides which bind bacterial cells without evident harm; 2) Peptides which bind bacterial cells and kill either by disrupting the membrane or blocking synthesis of membrane components, proteins, DNA and/or RNA; and 3) Peptides which do not interact with bacterial cells. In order to make our technology more informative, we have developed a procedure for distinguishing those classes of peptides directly on the microarray (see FIG. 1c). Using the intracellular stain CTO we detected the first class (peptide-binders) and the third class (no activity). We decided to involve additional reference dye "Alexa Fluor-555" with an NHS ester active group that attack free amines present in membrane-bound proteins. It was expected, and subsequently shown, that peptide-binders should have signals dominated by both dyes on parallel arrays (profile CTO+AF+). In the case of peptides with killing activity, CTO should leak out of cells once the membrane is disrupted (profile CTO−AF+).

Figure 3A:
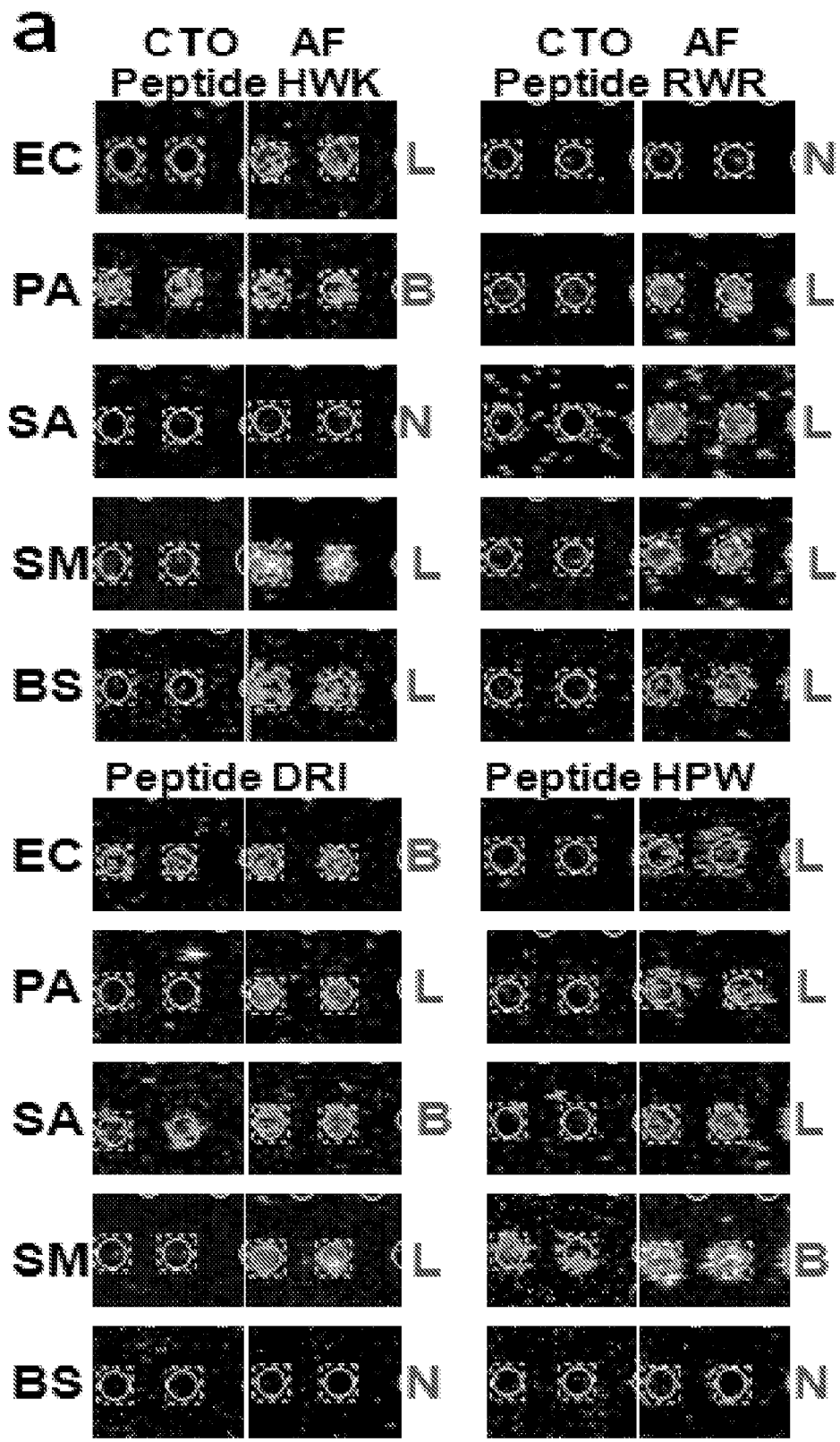
FIG. 3. Efficacy of functional assay (see scheme on FIG. 1a) for distinguishing of binding and lytic peptides directly on microarray (a, b). (a) Microarray patterns of CTO stained vs AlexaFluor labeled *E. coli* (EC), *P. aeruginosa* (PA), *S. aureus* (SA), *S. mutans* (SM) and *B. subtilis* (BS) at the peptides HWK, RWR, DRI, HPW (spotted in duplicates). L—lytic peptide with microarray profile "CTO−AF+". B—binding peptide "CTO+AF+". N—no microarray profile. (b) AF555-NHS labeled EC, PA, SA, SM (x axis) plotted versus themselves in competition with 20× excess of non-labeled cells (y axis). Both axes show raw median fluorescent signal at 543 nm on a logarithmic scale. Green lines delimit the twofold change. Annotated dark dots are peptide-binders detected previously with CTO for each strain specifically. Peptides are classified "Binders" if repeated with AF (CTO+AF+) out of twofold compared to negative control. Other peptides in this area (red dots) have profile "CTO−AF+" and classified "Lytic". (c) Specificity and uniqueness of bacterial profiles at random sequence peptide microarray. Heatmap (1) compares the intensities of EC peptide-binders (CTO+AF+profile) with PA, SA, SM and BS (blue: low; red: high). CTO/AF 555 fluorescent intensity, log 2, median with subtracted background. Venn diagrams show the numbers of unique and common binding (2) and lytic (3) peptides for different strains.

The examples of microarray profiles of CTO and AF labeled cells of EC, PA, SA, SM and BS at certain peptides are presented on FIG. 3a. It is clearly seen on the microarray images that profiles of binding peptides (CTO+AF+) could be unambiguously distinguished from profile of lytic peptides (CTO−AF+) (FIG. 3a).

Figure 3B:
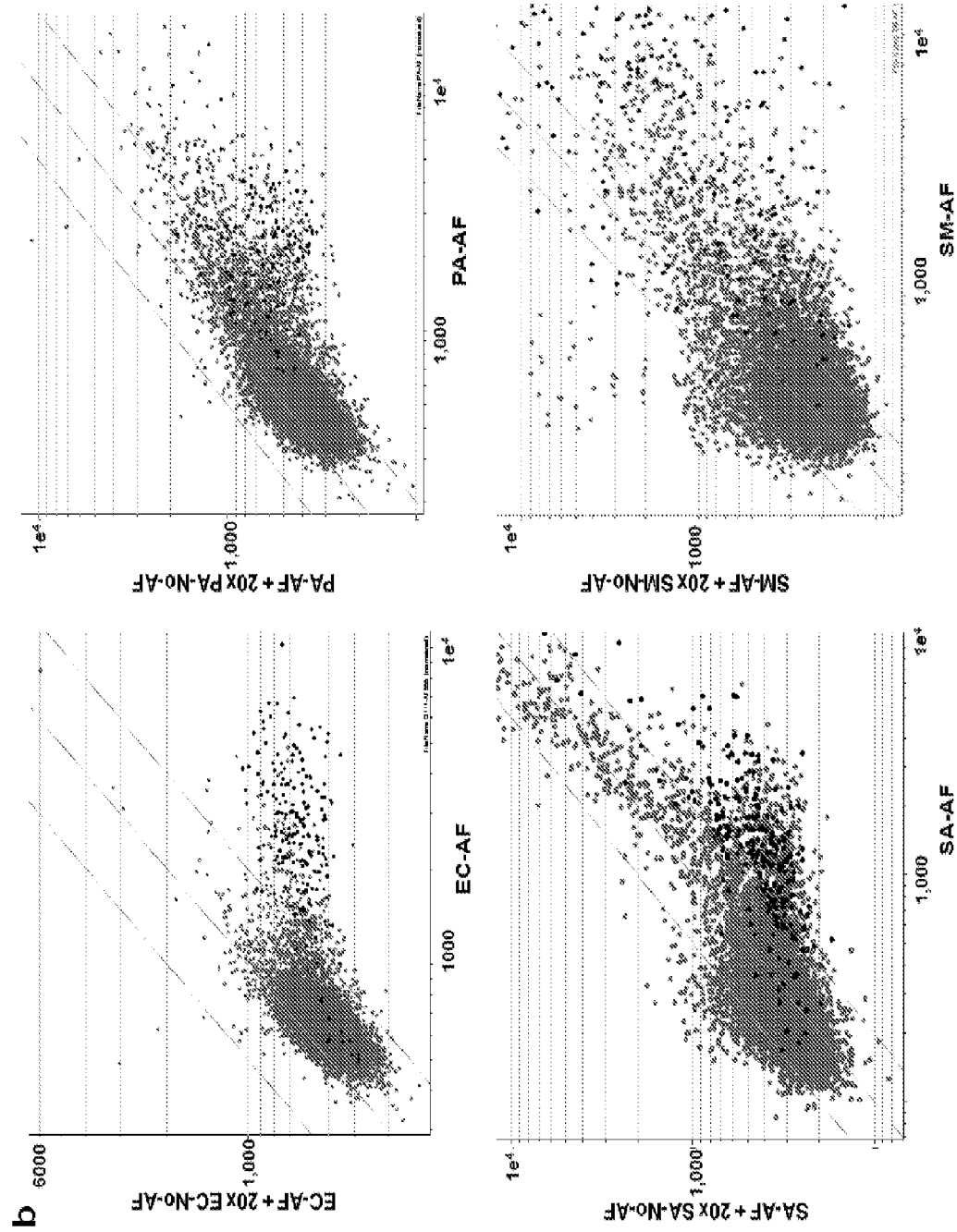
Figure 3C:
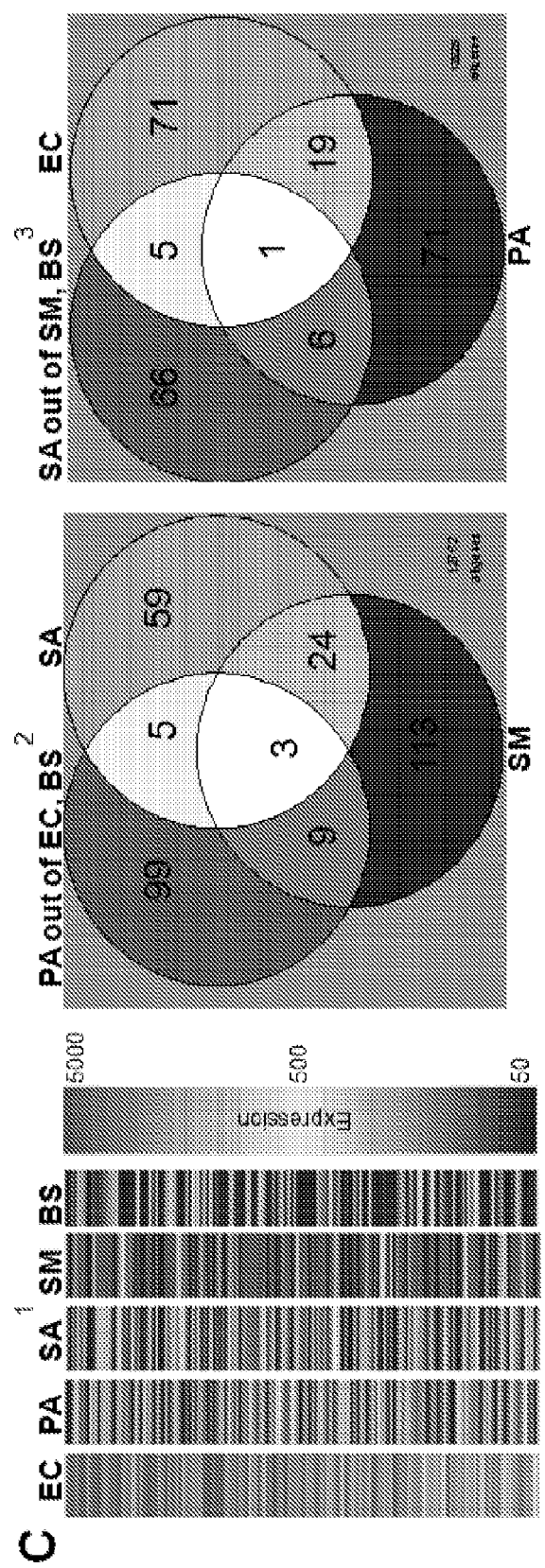

In order to demonstrate performance capacity of the functional assay with all 10K peptides, we have examined the list of peptide-binders (CTO+) for each pathogen on scatter plots with AF intensities (FIG. 3b). Most peptide-binders found with CTO (black filled circles), were also seen in the AF+ data (signals>2 fold versus competition assay extending along x-axis, FIG. 3b). They were assigned the profile "CTO+AF+" and subsumed in the binder-candidates category. However, there are additional signals (red filled circles) in this AF+ area which may also have lytic activity, otherwise they would be detected with CTO (see FIG. 1c). This group was assigned the profile "CTO−AF+" and taken into the antimicrobial candidates category. A few annotated peptides (black filled circles) within 2-fold change were ignored as CTO false positive signals.

These data support our idea to distinguish lytic and binding peptides directly from the microarray profile. One of the main advantages of our protocol is detection both antimicrobial and binding peptides in HTP without need for additional transformation of bacteria.

Using this approach 100-150 peptides with profile "CTO+AF+" and 50-100 peptides with profile "CTO−AF+" for each strain as candidates for binding and antimicrobial peptides were identified (data not shown). Note that some overlap in properties binder/lytic is possible when signal ratio AF/CTO is exceeding 1.5 for the peptide classified as binders and getting less than 2 for lytic peptides.

To illustrate whether the 10K peptide library is sufficient to distinguish different bacteria, we displayed fluorescent intensity at each peptide as a color-coded bar graph. FIG. $3c_1$ shows the list of binders for EC compared to PA, SA, SM and BS; this is highly distinctive, a linear classifier had 0% error in distinguishing bacteria. Additionally by Venn diagrams (FIG. $3c_{2,3}$) the list of distinguishing peptides is unique per stain whether they are binders or lytic. In order to find unique binders, we selected peptides which bind PA specifically compared to EC and BS and analyzed them on diagram along with SA and SM (FIG. $3c_2$). In this way we obtained 99 unique binders for PA, 63 for EC, 58 for BS, 52 for SM, and 47 for SA. The same approach was applied for lytic peptides (example SA vs EC and PA on FIG. $3c_3$) yielding 66 unique lytic peptides for SA, 58 for SM, 54 for BS, 50 for EC, and 44 for PA.

It should be stressed that more common binding and lytic peptides were found within group of G+ (24 for SA/SM on FIG. $3c_2$) and G− (19 for EC/PA on FIG. $3c_3$) than between them (9 for PA/SM, 5 for PA/SA on FIG. $3c_2$; 5 for SA/EC, 6 for SA/PA on FIG. $3c_3$). Furthermore, we discovered just one common peptide-binder and one common lytic peptide for all five profiled strains (data not shown). It must be stressed that this analysis was done using two reference dyes which certainly increase the reliability of selection of therapeutic candidates. Based on these data, we conclude that our protocols are appropriate to get reproducible and, most importantly, distinct profiles of different bacterial strains.

In Vitro Validation of the Microarray Selected Peptides

To test whether we can extrapolate directly the microarray predicted binding/lytic activity of peptides to a solution phase and eventually to in vivo applications, we performed in vitro inhibition assays. (Table 1). For this purpose we have randomly re-synthesized 40 peptides at which EC, PA, SA, SM and BS had different profiles: "CTO+AF+" (peptide-binders), "CTO−AF+" (lytic) and "CTO−AF−" (no array profile).

It was encouraging to find that most of the peptides with predicted lytic activity inhibited the bacterial growth while peptides from "Binders" and "No array profile" groups had minor or no inhibition, or even enhanced growth. This trend continues on all tested peptides (Table 1). For EC mean inhibition in the group "CTO−AF+" is 71.7% vs 14% in "CTO+AF+", for PA 66.4% vs 16.5%, for SA 78.8% vs 14%, for SM 54% vs 34% and for BS 805% vs 33%.

To further confirm the microarray predicted properties of peptides, we plated bacterial cultures after mixing with lytic and binding peptides. Peptides with predicted antimicrobial activity inhibit the growth of bacteria while binders do not, with limited exceptions (ex: one peptide for EC which showed 83% inhibition in solution but no activity on the plates).

Analysis of the deviations from microarray predicted properties revealed certain regularity: the "CTO−AF+" peptide group shows decreasing antimicrobial activity with increasing probability to form a helix, which stands in contrast to general antimicrobial peptide database prediction[27]. Moreover, analysis of physical properties showed a clear distribution of tested peptides from binders to lytic when arranged by increasing order of charge or decreasing order of the probability to form a helix. These features, charge and helix, appeared to be alternative but not compensative in our application. This finding was encouraging as it provides a base for more precise post-microarray therapeutic candidate selection.

Enhancing of Antimicrobial Activity and Specificity by Making Bivalent Peptides

Figure 4:
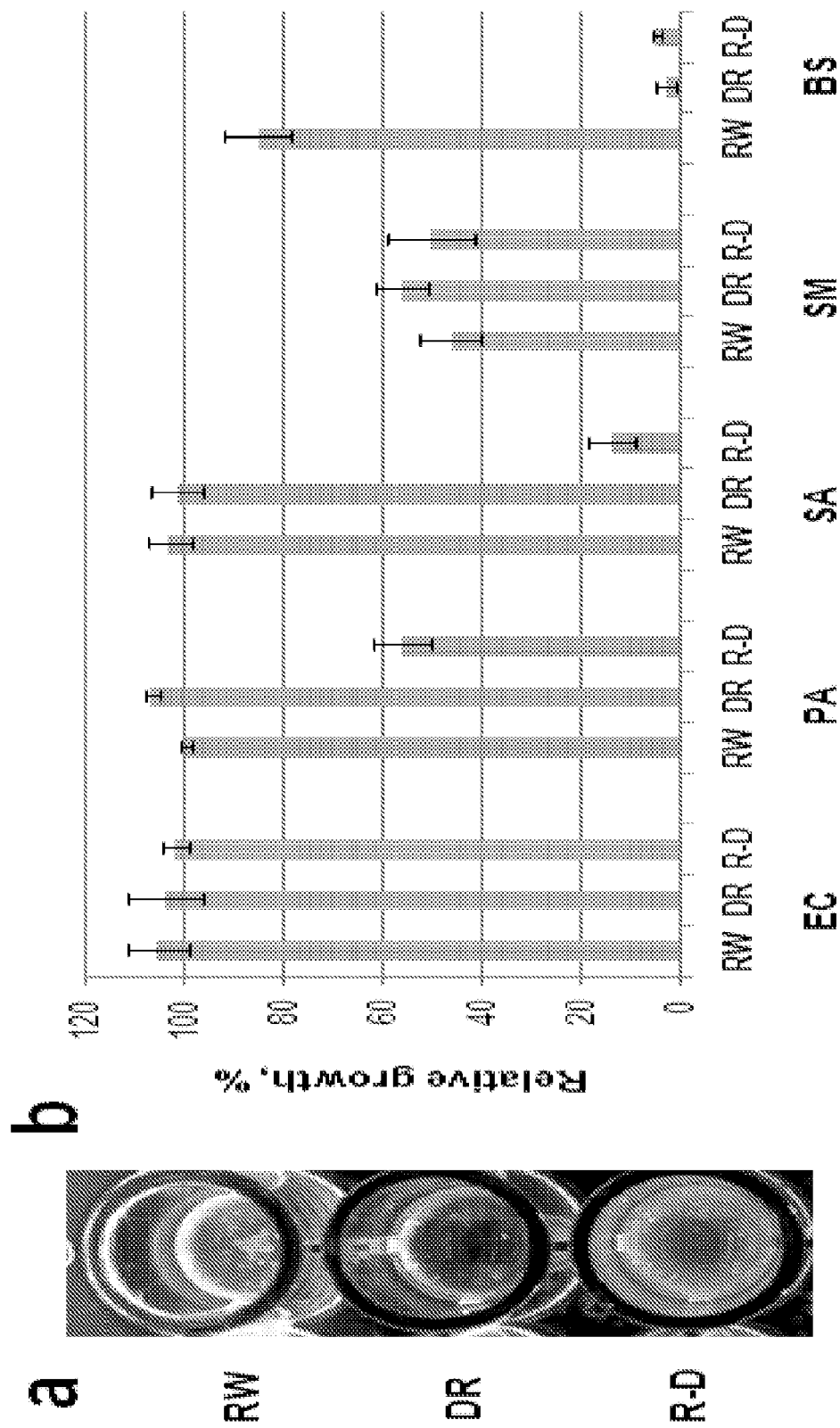
FIG. 4. Characteristic of bivalent compound "R-D". (a) Different properties of initial peptides RW and DR, and their lysine linked bivalent "R-D" at 100 uM in culture of *S. aureus* ($2 \times 10^5$ CFU/ml) right after adding. (b) Activity and specificity advantages of bivalent "R-D" over the initial peptides (RW and DR) against *S. aureus* (SA) compared to *E. coli* (EC), *P. aeruginosa* (PA), *S. mutans* (SM) and *B. subtilis* (BS). End-point measurement after 18 h incubation.

Microarray based identification of lytic and binding peptides described above laid the foundation for selection of pathogen specific candidates for new therapeutics. As a result, a database of binding and lytic peptides was created for each strain. We engaged this database in the design of dual-function antimicrobial agents by analogy with[29,30]. Initially we sought increased specificity and activity of strong antimicrobial peptides (lytic) by conjugation with peptides that were strong species-specific binders. We designed bivalent dual-function compound "R-D" which consisted of broad spectra antimicrobial (RW) (RWRRH-KHFKRPHRKHKRGSC (SEQ ID NO: 1)) and binding (DR) (DRIFHKMQHKPYKIKKRGSC (SEQ ID NO: 2)) peptides for *Staphylococcus aureus* UAB637. The profile combination "lytic/binder" of peptides RW/DR is specific for SA only while both are lytic for PA and SM, EC has profile "no profile/binder" and BS has profile "lytic/no profile" at those peptides. Peptide RW is positively charged (+14), peptide DR is "+8" but has helix potential with three evenly-spaced hydrophobic residues on the same surface. A difference in properties of starting peptides and bivalent "R-D" was seen by naked eye immediately after adding them to cell culture (FIG. 4a).

Results of in vitro assays showed an 80% stronger inhibition effect of bivalent "R-D" against SA and 50% against PA compared to original peptides (FIG. 4b) at 25 uM for DR, 20 uM for RW and 15 uM for "R-D". MIC determination demonstrated twice enhanced antimicrobial activity of bivalent "R-D" compared to the lead peptide RW against SA and ~1.2 times for PA. Measuring the bactericidal kinetics of RW, DR and bivalent "R-D" over time shows the advantage of the last one starting already at 8 h incubation (data not shown).

Discussion

We propose a method for developing pathogen specific synthetic antibodies: (i) Screening of bacteria with random sequences peptide microarrays (1K and above); (ii) Selection of specific binding and antimicrobial peptides; (iii) Making dual function synthetic antibodies by linking the microarray selected peptides with different properties.

We have designed a hyperbranched polymer surface chemistry which minimized non-specific binding of bacteria to the microarray surface and available functional groups and increased the density of immobilized peptides (FIG. 1a). Combination of these microarrays with proper labeling in binding assays and correct negative controls in competition assay helped to better distinguish uniquely 12 different bacteria (5 reported here: *E. coli* O111:B4, *P. aeruginosa* PAO-1, *S. aureus* UAB637, *S. mutans* UAB147, *B. subtilis*), and 18 viruses to the point that if given one of these as an unknown we stood a >99.9% chance of identifying them solely by the pattern of peptides that they bound. Such results give us strong belief that our strategy is applicable for any pathogen. An additional advantage of our microarray is relatively big library (10,000) of random peptides which could potentially supply enormous numbers of combinations and permutations of APs none of which been evolutionary optimized and unlikely to be highly toxic. The 20-mer peptides are unusually long compared to other high-throughput techniques. The potential for finding binding peptides is fairly high considering the total number of amino acid combinations that can be simultaneously interrogated.

Figure 1C:
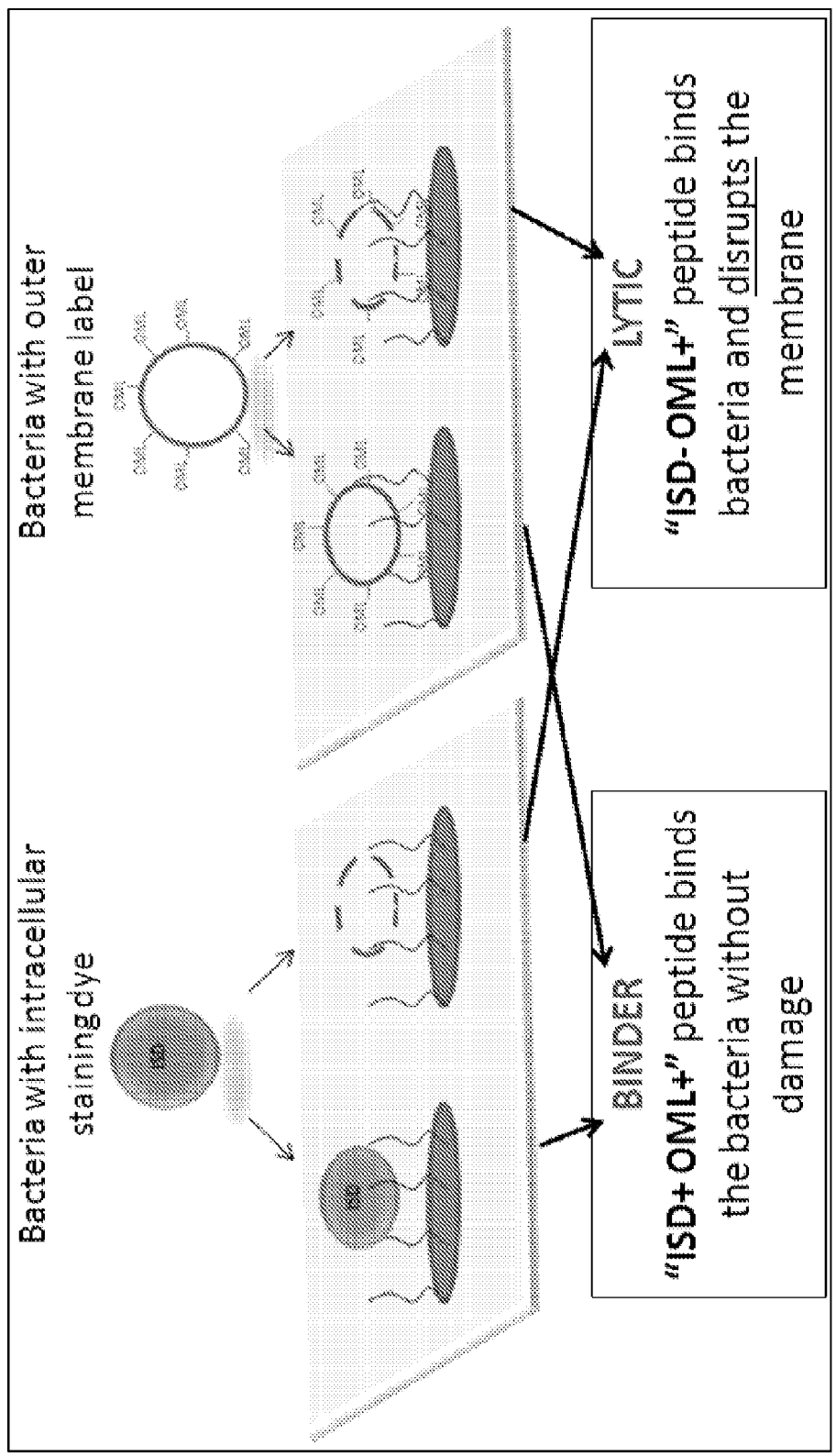

Another objective was to find a way for distinguishing between the antimicrobial and targeting properties of peptides directly on the microarray. To this end, we developed the procedure for functional differentiation of peptides based on a combination of intracellular stain (CTO) and membrane label (AF555-NHS ester) (FIGS. 1c, 3a, b). Thus not only specific binding peptide can be selected from microarray as candidates for synthetic antibodies, but also lytic peptides which allows maximal use of random peptides library potential in our technology. It should be stressed that there is currently no similar procedure. Our technology poses several critical advantages: (i) Dual dye functional assay allows direct detection of lytic peptides as well as peptide-binders on microarray; (ii) 10K peptides library has >70% purity and 100% correct sequences; (iii) 20-mer peptides are more likely to have antimicrobial activity than shorter peptides; (iv) The sensitivity from using the hyperbranched polymer yields ~5 times higher efficiency of binding and which can be recapitulated in solution; (v) There is no need for transformation the bacteria with additional genes, with our labeling procedure any bacteria could be profiled in as little as 2 hours; (vi) Glass microarrays are stable and reasonably inert.

The microarray predicted peptide properties translated well into solution-phase, a results that was certainly not a given. For example, peptides with microarray predicted lytic activity showed more that 70% inhibition (average between 5 strains) in vitro.

Peptides identified as binders from the array might have inhibition in vitro. This issue was not as concerning as one might expect; there was only 27% of peptide-binders among all five strains (Table 1) with 22.3% growth inhibition (mean) compared to 70.3% of lytic peptides. Having the reliable protocol for selection of specific targeting and antimicrobial peptides we were able to create antimicrobial synthetic antibodies with increased specificity that would avoid killing benign and beneficial commensalls. Specifically, two peptides classified on microarray as "lytic" and "strong binder" for S. aureus were covalently linked to the lysine scaffold. The new bivalent compound "R-D" showed ~2-fold antimicrobial activity against S. aureus vs. unlinked peptides. This antimicrobial dual-function synthetic antibody, designed based on the microarray data, showed a clear advantage over the component peptides even in end-point measurement assay. In general, our strategy allows selection of peptides for synthetic antibodies either for direct killing or targeting certain pathogen for activation of the humoral immune system.

The unique combination of bacterial profiling on a microarray with subsequent selection of binding vs. lytic peptides enables a very straightforward process for selection of pathogen specific therapeutic candidates. The ability to create a specific synthetic antibody based on a pathogen's microarray profile that merges two or more peptide characteristics is fundamentally new to the antimicrobial field and is potentially paradigm-shifting.

Inhibition assays and MIC determinations were conducted according to the Clinical and Laboratory Standard[41] in Mueller-Hinton (MH; Fisher) broth medium at 35±2° C. for EC, BS, PA, SA; in MH II (cation adjusted) with 5% horse blood for SM.

CFU number controls and survivors control in bactericidal kinetics were conducted in MH agar for EC, BS, PA, SA; in MH II agar with 5% sheep blood for SM.

Peptide Microarray Design and Construction:
Protocol was described in details previously in[31].

Peptide Microarray Surface Chemistry:
It was assumed, due to the bigger size of cells compared to regular targets (proteins), that we need higher density of peptides immobilized to the array to ensure the efficient interaction with bacterial membranes. We developed the special surface chemistry involving hyperbranched polymer (FIG. 1a).

Polymer coating also allows minimizing the surface effects on the peptides conformation, properties and availability. The procedure includes: 1) Cleaning of glass slides

TABLE 1

Summarized results of in vitro activity test of the microarray selected peptides

| Strains | CTO+AF+ | | | | CTO−AF+ | | | |
|---|---|---|---|---|---|---|---|---|
| | Total number of peptides | ↓ | ↑ | N | Total number of peptides | ↓ | ↑ | N |
| EC | 11 | 2 (14%) | 4 (8.5%) | 5 | 11 | 6 (71.7%) | 2 (8%) | 3 |
| PA | 17 | 4 (16.5%) | 7 (6.4%) | 6 | 14 | 8 (66.4%) | 2 (4.5%) | 4 |
| SA | 8 | 2 (14%) | 6 (21.7%) | — | 8 | 6 (78.8%) | 1 (8%) | 1 |
| SM | 22 | 7 (34%) | 14 (85.8%) | 1 | 12 | 7 (54%) | 4 (57.5%) | 1 |
| BS | 4 | 2 (33%) | 2 (26%) | — | 15 | 14 (80.5%) | — | 1 |

↓—number of peptides inhibiting bacterial growth at 100 uM (% inhibition, average);
↑—number of peptides enhancing bacterial growth (% enhancing, average);
N—no detected activity.

Methods

Unless noted otherwise, all chemicals were purchased from Sigma-Aldrich Inc. (Milwaukee, Wis., USA) and used without further purification. Deionized water was obtained from a Millipore ultrapure water filtration unit. Microarray peptides were synthesized by Alta Biosciences Ltd. (Birmingham, UK). Lead peptides were resynthesized in-house by using Fmoc chemistry and purified to 95% by HPLC. Spectrophotometric measurements were carried out by using a NanoDrop® ND-1000, SpectraMax 190 and M5 (Molecular Devices). Microarrays were scanned with ProScanArray HT microarray scanner (Perkin Elmer).

Strains and Growth Conditions:
For the microarray screening assay Escherichia coli O111:B4 (EC) (ATCC) was grown at 37° C. in Difco nutrient broth medium for non-fastidious organisms (Becton, Dickinson and Company 231000). Bacillus Subtilis (BS) 1A423, Pseudomonas aeruginosa (PA) PAO-1 and Staphylococcus aureus (SA) UAB637 (kindly provided by Center for Infectious Diseases and Vaccinology (CIDV), the Biodesign Institute at Arizona State University (ASU)) were grown at 37° C. in Luria-Bertani broth medium (LB, Fisher) under aerobic conditions. Streptococcus mutans UAB147 Serotype C (kindly provided by CIDV, ASU) was grown at 37° C. in Todd-Hewitt (TH, Fisher) broth medium with 5% yeast extract under anaerobic conditions.

by Piranha solution (70:30 v/v mixture of concentrated $H_2SO_4$ and 30% $H_2O_2$) for at least 1 h at low rotation, followed by rinsing with $H_2O$ and drying; 2) Silanization in 1% solution of 3-glycidoxypropyl-trimethoxysilane in anhydrous toluene for 30 min at 40° C., followed by washing with toluene (3 times); 3) Curing for 40 min. at 120° C.; 4) Coating the slides with solution of 6 mg/ml polyethylenimine in 10% ethanol for 1 h at RT with agitation; 5) Reaction with sulfo-SMCC (Pierce Biotechnology, Rockford, Ill., USA; Cat#22622) to create a maleimide-activated surface; 6) Peptide immobilization by contact printing on pre-activated slides. The maleimide-activated surface reacts with the sulfhydryl group on the peptide's terminal cysteine.

Microarray Probing:
Before probing, the slides were treated with 90% TFA (trifluor-acetic acid) to get rid of non-immobilized peptides, blocking groups and probable organic impurities followed by DMF, ethanol and deionized water washing. Then, the slides were placed in a humidified chamber and blocked for 1 h at room temperature with buffer (3% BSA, 0.014% mercaptohexanol and 0.05% Tween-20 in 1×TBS).

Turbidity of overnight cultures was measured at $OD_{600}$. The CFU/ml value was calculated according to McFarland turbidity standard. Cell cultures were diluted to $8×10^8$ and washed 2 times with 1×PBS buffer with 0.05% FBS (Fetal Bovine Serum, Invitrogen 10091-130). CTO staining solution was prepared by adding 500 μl of pre-warmed appropriate media with 10 uM CTO to one tube of washed cells and incubated in foil wrapped tube for 1 h at 37° C. at 250 rpm. Alexa Fluor 555 NHS ester (Invitrogen A32755) labeling solution was prepared by adding the 500 ul of 1×TBS/FBS with the content of one pre-packed dye vial dissolved in 10 ul DMSO to washed cells. Sample was incubated in a foil wrapped tube for 1 h at RT with agitation. After staining/labeling, cells were washed with 1×TBS/FBS. Amount of dyes and incubation times vary for different pathogens and needed to be found experimentally.

After blocking the slides were washed with 1×TBS-T (1×30 inversion in a Coplin jar) and ddH$_2$O (3×30 inversions in a Coupling jar). The slides were then dried by centrifugation at 1500 rpm for 2 min. The Agilent hybridization chamber was then used to ensure the interaction of the solution (10$^8$ labeled cells in 1×TBS with 0.03% Sodium azide, 3% BSA and 0.05% Tween 20 in total 450 ul) with the microarrays. To subtract false positive non-specific signals driven by dyes binding, we conducted competitions with 20× excess of un-labeled cells. For Gram negative strains we also performed competition with 100× excess of free LPS.

Each microarray probing was performed in triplicate. The slides were incubated for 1 h at 37° C. in the rotator (Agilent Technologies). Then slides were washed with 1×TBS-T (3×30 inversions in a Coplin jar) and ddH$_2$O (3×30 inversions in a Coplin jar); the solution was changed each time. Finally, the slides were dried by centrifugation at 1500 rpms for 2 min and scanned.

Microarray Scanning and Data Analysis:

Microarrays were scanned by using a Perkin-Elmer ProScanArray HT Microarray Scanner with the 488, 543 and 633 nm excitation lasers at 100% power and 70% photomultiplier tube gain. Detection was done at 570 nm for Cell Tracker Orange and AF555, at 508 nm for SYTO 9 and at 670 nm for DRAQS. All scanned images were analyzed by using GenePix Pro 6.0 software (Axon Instruments, Union City, Calif., USA). Upon careful visual inspection, bad spots were eliminated by flagging them absent. Median spot intensities were used in further analyses. Image-processed data were imported from GenePix for the following statistical analysis of microarray data to GeneSpring 7.2 (Agilent, Inc., Palo Alto, Calif., USA). For correct analysis, each slide was normalized either to 50th percentile or by subtracting the local background from median intensity at each spot. Measurements of less than 0.01 were set to 0.01. The microarray profiles collected for each bacterial strain were compared by using scatter plots as previously reported by[31,33]. Binding assay data were plotted versus competition assay data for each dye separately. The only peptides that demonstrated at least 2 times higher intensity in binding assay were considered in the followed analysis. Peptides differentiated by statistical means had been also inspected visually back on the slides. Peptides with microarray profile "presence" at both CTO and AF555 dyes (CTO+AF+) were considered as binders. Lytic peptides were selected as those with microarray profile "absence" at CTO and "presence" at AF555 dyes (CTO−AF+) (FIG. 1c).

In order to distinguish specific peptide-binders and APs candidates the profiles of different strains were compared by Venn diagrams.

Fluorescent Microscopy:

For the microscopic detection of bacterial adhesion to the peptide microarray we printed custom slides with 10-20 peptides of interest. All procedures of microarray preparation and processing were the same as described above. After last washing and drying, the 50 ul of 1×PBS were applied to the slides and spread under the cover slip. Binding was evaluated using fluorescent microscopy (Olympus BX61), at ×60 magnification with immersion oil with Cy3 excitation laser. Digital images were collected using factory-supplied software DP Controller 2.2.1.227 Olympus Corporation.

Synthesis of Synthetic Antibodies:

Protocol "Branched lysine scaffold". Bivalent synbody was synthesized via a modified divergent solid phase peptide synthesis using Fmoc-Lys(ivDde)-OH as the scaffold using the protocols outlined in[14]. Synthesis was performed by removal of the Fmoc-protecting group followed by synthesis of peptide 1 on α-amino group of Lysine through stepwise addition of Fmoc amino acids. Upon completion of peptide 1 synthesis, the N-terminal Fmoc group was substituted with Boc group prior to deprotection of the Nε-(ivDde) protecting group. The stepwise assembly of peptide 2 was then accomplished at Nε-lysine position using stepwise addition of Fmoc-protected amino acids on the peptide synthesizer. The final protected synbody was treated with cleavage cocktail for 2 hrs at room temperature and precipitated in cold diethyl ether. The solid was separated from diethyl ether by centrifugation and the top phase decanted off and pellet resuspended with another addition of dry diethyl ether. The cooling and centrifugation processes were done in triplicate, as the construct was dried and dissolved in water for HPLC purification. Finally, the synbody was purified by HPLC and quality was analyzed by MALDI mass spectrometry. The antimicrobial bivalent peptide was designed with peptides connected to the linker via C-terminuses.

REFERENCES

1. Wickens, K. et al. The association of early life exposure to antibiotics and the development of asthma, eczema and atopy in a birth cohort: confounding or causality? *Clinical & Experimental Allergy* 38, 1318-1324 (2008).
2. Blaser, M. Antibiotic overuse: Stop the killing of beneficial bacteria. *Nature* 476, 393-394 (2011).
3. Chambers, H. F. & DeLeo, F. R. Waves of resistance: *Staphylococcus aureus* in the antibiotic era. Nat Rev Micro 7, 629-641 (2009).
4. Hawkey, P. M. & Jones, A. M. The changing epidemiology of resistance. *Journal of Antimicrobial Chemotherapy* 64, i3-i10 (2009).
5. Teuber, M. Veterinary use and antibiotic resistance. *Current Opinion in Microbiology* 4, 493-499 (2001).
6. Cohen, M. L. Epidemiology of Drug Resistance: Implications for a Postâ€" Antimicrobial Era. *Science* 257, 1050-1055 (1992).
7. Kim, S. & Aga, D. S. Potential Ecological and Human Health Impacts of Antibiotics and Antibiotic-Resistant Bacteria from Wastewater Treatment Plants. *Journal of Toxicology and Environmental Health, Part B* 10, 559-573 (2007).
8. Silver, L. L. & Bostian, K. A. Discovery and development of new antibiotics: the problem of antibiotic resistance. *Antimicrob. Agents Chemother.* 37, 377-383 (1993).
9. Casadevall, A. Crisis in Infectious Diseases: Time for a New Paradigm? *Clinical Infectious Diseases* 23, 790-794 (1996).
10. Casadevall, A. The case for pathogen-specific therapy. *Expert Opinion on Pharmacotherapy* 10, 1699-1703 (2009).

11. Legutki, J. B., Magee, D. M., Stafford, P. & Johnston, S. A. A general method for characterization of humoral immunity induced by a vaccine or infection. *Vaccine* 28, 4529-4537 (2010).
12. Saylor, C., Dadachova, E. & Casadevall, A. Monoclonal antibody-based therapies for microbial diseases. *Vaccine* 27, G38-G46 (2009).
13. Reichert, J. M. & Dewitz, M. C. Anti-infective monoclonal antibodies: perils and promise of development. *Nat Rev Drug Discov* 5, 191-195 (2006).
14. Diehnelt, C. W. et al. Discovery of High-Affinity Protein Binding Ligands—Backwards. *PLoS ONE* 5, e10728 (2010).
15. Yeaman, M. R. & Yount, N. Y. Mechanisms of Antimicrobial Peptide Action and Resistance. *Pharmacological Reviews* 55, 27-55 (2003).
16. Zhang, L. et al. Antimicrobial Peptide Therapeutics for Cystic Fibrosis. *Antimicrob. Agents Chemother.* 49, 2921-2927 (2005).
17. Bradshaw, J. P. Cationic Antimicrobial Peptides: Issues for Potential Clinical Use. *BioDrugs* 17, 233-240 (2003).
18. Sitaram, N. & Nagari, R. Host-defense Antimicrobial Peptides: Importance of Structure for Activity. *Current Pharmaceutical Design* 8, 727-742 (2002).
19. Dhople, V., Krukemeyer, A. & Ramamoorthy, A. The human beta-defensin-3, an antibacterial peptide with multiple biological functions. *Biochimica et Biophysica Acta (BBA)—Biomembranes* 1758, 1499-1512 (2006).
20. Zasloff, M. Magainins, a class of antimicrobial peptides from *Xenopus* skin: isolation, characterization of two active forms, and partial cDNA sequence of a precursor. *Proceedings of the National Academy of Sciences* 84, 5449-5453 (1987).
21. Sawai, M. V. et al. Impact of single-residue mutations on the structure and function of ovispirin/novispirin antimicrobial peptides. *Protein Engineering* 15, 225-232 (2002).
22. Srinivas, N. et al. Peptidomimetic Antibiotics Target Outer-Membrane Biogenesis in *Pseudomonas aeruginosa*. *Science* 327, 1010-1013.
23. Chou, H.-T. et al. Design and synthesis of cationic antimicrobial peptides with improved activity and selectivity against *Vibrio* spp. *International Journal of Antimicrobial Agents* 32, 130-138 (2008).
24. Gordon, Y. J., Romanowski, E. G. & McDermott, A. M. A Review of Antimicrobial Peptides and Their Therapeutic Potential as Anti-Infective Drugs. *Current Eye Research* 30, 505-515 (2005).
25. Cudic, M. et al. Development of novel antibacterial peptides that kill resistant isolates. *Peptides* 23, 2071-2083 (2002).
26. Tencza, S. B. et al. Lentivirus-derived antimicrobial peptides: increased potency by sequence engineering and dimerization. *Journal of Antimicrobial Chemotherapy* 44, 33-41 (1999).
27. Wang, G., Li, X. & Wang, Z. APD2: the updated antimicrobial peptide database and its application in peptide design *Nucleic Acids Research* 37, D933-D937 (2009).
28. Hancock, R. E. W. & Sahl, H.-G. Antimicrobial and host-defense peptides as new anti-infective therapeutic strategies. *Nat Biotech* 24, 1551-1557 (2006).
29. Eckert, R. et al. Adding Selectivity to Antimicrobial Peptides: Rational Design of a Multidomain Peptide against *Pseudomonas* spp. *Antimicrob. Agents Chemother.* 50, 1480-1488 (2006).
30. He, J. et al. Systematic Approach to Optimizing Specifically Targeted Antimicrobial Peptides against *Streptococcus mutans*. *Antimicrob. Agents Chemother.* 54, 2143-2151 (2010).
31. Morales, C. et al. Bacterial Glycoprofiling by Using Random Sequence Peptide Microarrays. *ChemBioChem* 10, 877-888 (2009).
32. Halperin, R. F., Stafford, P. & Johnston, S. A. Exploring Antibody Recognition of Sequence Space through Random-Sequence Peptide Microarrays. *Molecular & Cellular Proteomics* 10 (2010).
33. Reddy, M. M. & Kodadek, T. Protein "fingerprinting" in complex mixtures with peptoid microarrays. *Proceedings of the National Academy of Sciences of the United States of America* 102, 12672-12677 (2005).
34. Hilpert, K., Volkmer-Engert, R., Walter, T. & Hancock, R. E. W. High-throughput generation of small antibacterial peptides with improved activity. *Nat Biotech* 23, 1008-1012 (2005).
35. Hilpert, K. et al. Screening and Characterization of Surface-Tethered Cationic Peptides for Antimicrobial Activity. *Chemistry & Biology* 16, 58-69 (2009).
36. Hsu, K.-L., Pilobello, K. T. & Mahal, L. K. Analyzing the dynamic bacterial glycome with a lectin microarray approach. *Nat Chem Biol* 2, 153-157 (2006).
37. Disney, M. D. & Seeberger, P. H. The Use of Carbohydrate Microarrays to Study Carbohydrate-Cell Interactions and to Detect Pathogens. *Chemistry & Biology* 11, 1701-1707 (2004).
38. Falsey, J. R., Renil, M., Park, S., Li, S. & Lam, K. S. Peptide and Small Molecule Microarray for High Throughput Cell Adhesion and Functional Assays. *Bioconjugate Chemistry* 12, 346-353 (2001).
39. Palacios, G. et al. Panmicrobial oligonucleotide array for diagnosis of infectious diseases. *Emerging infectious diseases* 13, 73-81 (2007).
40. Liu, T.-T. et al. A High Speed Detection Platform Based on Surface-Enhanced Raman Scattering for Monitoring Antibiotic-Induced Chemical Changes in Bacteria Cell Wall. *PLoS ONE* 4, e5470 (2009).
41. CLSI Methods for dilution antimicrobial susceptibility tests for bacteria that grow aerobically; *Approved standard-Eight Edition*. CLSI document M07-A8. Wayn, PA: Clinical and Laboratory Standards Institute. 26 (2009).

We claim:

1. A method for identifying lytic polypeptides, comprising
(a) contacting one or more addressable polypeptide arrays with:
(i) a first population of cells of interest comprising an intracellular detectable marker (IDM); and
(ii) a second population of the cells of interest comprising a cell surface detectable marker (CSDM);
wherein the addressable polypeptide arrays comprise at least 1000 polypeptides of between 15-24 amino acids in length in defined locations on the array(s), and wherein the contacting occurs under conditions suitable to promote binding of polypeptides to the cells of interest; and
(b) detecting binding of the polypeptides to the cells of interest; wherein a polypeptide that binds cells in the first population of cells without damage to the cells and binds cells in the second population of cells without damage to the cells is a binding polypeptide for the cells of interest; and wherein a polypeptide that binds cells in the first population of cells with damage to the cells and binds cells in the second population of cells with damage to the cells is a lytic polypeptide for the cell of interest.

2. The method of claim 1, wherein method comprises using at least two polypeptide arrays, wherein the first population of cells is contacted to the first polypeptide array and the second population of cells is contacted to the second polypeptide arrays.

3. The method of claim 1, wherein the cells are pathogenic cells.

4. The method of claim 3, wherein the pathogenic cells are selected from the group consisting of bacterial cells, protozoan cells, fungal cell, and helminth cells.

5. The method of claim 1, further comprising preparing a synthetic antibody by linking
(a) a binding polypeptide for a cell of interest; and
(b) a lytic polypeptide for the cell of interest.

6. The method of claim 1, wherein a surface of the addressable polypeptide arrays is functionalized by a process comprising:
(i) treating the surface with 3-glycidoxypropyl-trimethoxysilane to create a treated surface;
(ii) reacting the treated surface with hyperbranched polyethylenimine to create a reacted surface; and
(iii) further reacting the surface with heterobifunctional crosslinker succinimidyl-4-(N-maleimidomethyl)cyclohexane-1-carboxylate;
wherein the polypeptides are bound to the functionalized surface.

7. The method of claim 1, wherein the IDM is a fluorescent chloromethyl derivative.

* * * * *